(12) United States Patent
Biris et al.

US012201746B2

(10) Patent No.: US 12,201,746 B2
(45) Date of Patent: Jan. 21, 2025

(54) EXPANDABLE BONE AND TISSUE REGENERATION SYSTEM, AND APPLICATIONS OF SAME

(71) Applicant: BOARD OF TRUSTEES OF THE UNIVERSITY OF ARKANSAS, Little Rock, AR (US)

(72) Inventors: Alexandru S. Biris, Little Rock, AR (US); Karrer M. Alghazali, Little Rock, AR (US); Anwer Dheyaa Mahdi Mhannawee, Little Rock, AR (US)

(73) Assignee: BOARD OF TRUSTEES OF THE UNIVERSITY OF ARKANSAS, Little Rock, AR (US)

(*) Notice: Subject to any disclaimer, the term of this patent is extended or adjusted under 35 U.S.C. 154(b) by 244 days.

(21) Appl. No.: 16/783,256

(22) Filed: Feb. 6, 2020

(65) Prior Publication Data

US 2021/0244854 A1    Aug. 12, 2021

(51) Int. Cl.
| | |
|---|---|
| A61L 27/36 | (2006.01) |
| A61L 27/04 | (2006.01) |
| A61L 27/08 | (2006.01) |
| A61L 27/12 | (2006.01) |
| A61L 27/20 | (2006.01) |
| A61L 27/24 | (2006.01) |
| A61L 27/38 | (2006.01) |
| A61L 27/56 | (2006.01) |
| B33Y 80/00 | (2015.01) |

(52) U.S. Cl.
CPC .............. *A61L 27/365* (2013.01); *A61L 27/04* (2013.01); *A61L 27/08* (2013.01); *A61L 27/12* (2013.01); *A61L 27/20* (2013.01); *A61L 27/24* (2013.01); *A61L 27/3695* (2013.01); *A61L 27/38* (2013.01); *A61L 27/56* (2013.01); *B33Y 80/00* (2014.12); *A61L 2400/04* (2013.01); *A61L 2400/06* (2013.01); *A61L 2400/12* (2013.01); *A61L 2430/02* (2013.01)

(58) Field of Classification Search
USPC ........................................................ 424/423
See application file for complete search history.

(56) References Cited

U.S. PATENT DOCUMENTS

| | | | |
|---|---|---|---|
| 6,514,515 B1* | 2/2003 | Williams ............... | A61L 27/18 |
| | | | 424/501 |
| 2007/0083268 A1 | 4/2007 | Teoh et al. | |
| 2010/0168869 A1 | 7/2010 | Long et al. | |
| 2013/0218253 A1 | 8/2013 | Kaufmann et al. | |
| 2018/0250444 A1 | 9/2018 | Beduer et al. | |
| 2018/0289490 A1 | 10/2018 | Estes et al. | |
| 2019/0022279 A1* | 1/2019 | Alghazali ............... | A61F 2/28 |

FOREIGN PATENT DOCUMENTS

CN    109789020 A    5/2019

OTHER PUBLICATIONS

Al-namnam, N. M., Govindan, M., Lin, W., Oon, K., Hwi, K., Huat, C., & Cheong, W. (2017). An injectable poly (caprolactone trifumarate-gelatin microparticles) (PCLTF-GMPs) scaffold for irregular bone defects: Physical and mechanical characteristics. Materials Science & Engineering C, 72, 332-340. https://doi.org/10.1016/j.msec.2016.11.086.
Albrektsson, T., & Johansson, C. (2001). and osseointegration, 96-101.
Ceramics, M., & Dubok, V. A. (2001). Bioceramics—Yesterday, Today, Tomorrow.pdf (vol. 39, pp. 381-394).
Guelcher, S. A. (2008). Biodegradable Polyurethanes: Synthesis and Applications in Regenerative Medicine. Tissue Engineering Part B: Reviews, 14(1), 3-17. https://doi.org/10.1089/teb.2007.0133.
Hench, L. L., & Thompson, I. (2010). Twenty-first century challenges for biomaterials. Journal of the Royal Society Interface, 7(Suppl. 4). https://doi.org/10.1098/rsif.2010.0151.focus.
Hollister, S. J. (2005). No TitlePorous scaffold design for tissue engineering. Nature Materials, 4, 518-524. Retrieved from http://dx.doi.org/10.1038/nmat1421.
Hutmacher, D. W. (2000). Scaffolds in tissue engineering bone and cartilage. The Biomaterials Silver Jubilee Compendium (vol. 21). Woodhead Publishing Limited. https://doi.org/10.1016/B978-008045154-1.50021-6.
Iqbal, M., & Xiaoxue, S. A. (2009). A review on biodegradable polymeric materials for bone tissue engineering applications, 5713-5724. https://doi.org/10.1007/s10853-009-3770-7.
Jackson, B. K., Bow, A. J., Kannarpady, G., Biris, A. S., Anderson, D. E., Dhar, M., & Bourdo, S. E. (2018). Polyurethane/nano-hydroxyapatite composite films as osteogenic platforms. Journal of Biomaterials Science, Polymer Edition, 29(12), 1426-1443. https://doi.org/10.1080/09205063.2018.1464264.
Laurencin, C. T., Ambrosio, A. M. A., Borden, M. D., & Cooper, J. A. (1999). Tissue Engineering: Orthopedic Applications, 19-46.
Li, Y., Chen, S., Li, L., & Qin, L. (2015). ScienceDirect Bone defect animal models for testing efficacy of bone substitute biomaterials. https://doi.org/10.1016/j.jot.2015.05.002.

(Continued)

*Primary Examiner* — David J Blanchard
*Assistant Examiner* — Daniel F Coughlin
(74) *Attorney, Agent, or Firm* — Locke Lord LLP; Tim Tingkang Xia, Esq.

(57) ABSTRACT

The disclosure relates to an expandable scaffold and a method for fabricating the scaffold. The expandable scaffold includes a three-dimensional porous structure comprising a composite material composed by a first material and a second material. The 3D porous structure has a tunable expansion capacity. When applied in a liquid, the 3D porous structure may uptake the liquid and expand from an original volume to an expansion volume up to 1000 times of the original volume. The 3D porous structure may be formed by a plurality of layers of the composite material, and architecture and shape of the layers of the composite material are arranged in accordance with a shape and a size of the expansion volume. Applications of the scaffold may include a bone or soft tissue regeneration system or a bleed stopping device.

25 Claims, 9 Drawing Sheets

(56) References Cited

OTHER PUBLICATIONS

Nail, L. N., Zhang, D., Reinhard, J. L., & Grunlan, M. A. (2015). Fabrication of a Bioactive, PCL-based "Self-fitting" Shape Memory Polymer Scaffold, (October), 1-8. https://doi.org/10.3791/52981.

Nedomová, B., Budáčová, J., Frištáková, M., & Šagát, T. (2016). Arthrogryposis multiplex congenita z pohl'adu anésteziológa. Lekarsky Obzor, 65(12), 354-359. https://doi.org/10.1002/jor.

Qutachi, O., Vetsch, J. R., Gill, D., Cox, H., Scurr, D. J., Hofmann, S., ... Rahman, C. V. (2014). Acta Biomaterialia Injectable and porous PLGA microspheres that form highly porous scaffolds at body temperature, 10, 5090-5098. https://doi.org/10.1016/j.actbio.2014.08.015.

Rasperini, G., Pilipchuk, S. P., Flanagan, C. L., Park, C. H., Pagni, G., Hollister, S. J., & Giannobile, W. V. (2014). 3D-printed Bioresorbable Scaffold for Periodontal Repair. Journal of Denal Reseach, 94(9), 153-157. https://doi.org/10.1177/0022034515588303.

Rousseau, M., Anderson, D. E., Lillich, J. D., Apley, M. D., Jensen, P. J., & Biris, A. S. (2014). In vivo assessment of a multicomponent and nanostructural polymeric matrix as a delivery system for antimicrobials and bone morphogenetic protein-2 in a unicortical tibial defect in goats, 75(3).

Senatov, F. S., Zadorozhnyy, M. Y., Niaza, K. V, Medvedev, V. V, Kaloshkin, S. D., Anisimova, N. Y., . . . Yang, K. (2017). Shape memory effect in 3D-printed scaffolds for self-fitting implants, 93(May), 222-231. https://doi.org/10.1016/j.eurpolymj.2017.06.011.

Senturk, B., Cubuk, M. O., Ozmen, M. C., Aydin, B., Guler, M. O., & Tekinay, A. B. (2016). Inhibition of VEGF mediated corneal neovascularization by anti-angiogenic peptide nanofibers. Biomaterials. https://doi.org/10.1016/j.biomaterials.2016.08.045.

Xie, R., Hu, J., Hoffmann, O., Zhang, Y., Ng, F., Qin, T., & Guo, X. (2018). Self-fitting shape memory polymer foam inducing bone regeneration: A rabbit femoral defect study. https://doi.org/10.1016/j.bbagen.2018.01.013.

Xie, R., Hu, J., Ng, F., & Tan, L. (2016). High performance shape memory foams with isocyanate-modified hydroxyapatite nanoparticles for minimally invasive bone regeneration. Ceramics International. https://doi.org/10.1016/i.ceramint.2016.11.216.

Zhang, D., George, O. J., Petersen, K. M., Jimenez-vergara, A. C., Hahn, M. S., & Grunlan, M. A. (2014). Acta Biomaterialia A bioactive "'self-fitting'" shape memory polymer scaffold with potential to treat cranio-maxillo facial bone defects. Acta Biomaterialia, (August). https://doi.org/10.1016/j.actbio.2014.07.020.

Korean Intellectual Property Office, "International Search Report for PCT/US2020/016932", KR, Nov. 4, 2020.

CNIPA, "First Office Action for CN Application No. 202080095759.6", China, Mar. 4, 2023.

* cited by examiner

EXPANDABLE BONE AND TISSUE REGENERATION SYSTEM, AND APPLICATIONS OF SAME

STATEMENT AS TO RIGHTS UNDER FEDERALLY-SPONSORED RESEARCH

This invention was made with government support under Contract No. W81XWH-15-1-0666 awarded by the Department of Defense (DOD). The government has certain rights in the invention.

CROSS-REFERENCE TO RELATED PATENT APPLICATIONS

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference is individually incorporated by reference. In terms of notation, hereinafter, [n] represents the nth reference cited in the reference list. For example, [9] represents the ninth reference cited in the reference list, namely, Jackson, B. K., Bow, A. J., Kannarpady, G., Biris, A. S., Anderson, D. E., Dhar, M., & Bourdo, S. E. (2018). Polyurethane/nano-hydroxyapatite composite films as osteogenic platforms. Journal of Biomaterials Science, Polymer Edition, 29 (12), 1426-1443.

FIELD

The present disclosure relates generally to an expandable bone and tissue regeneration system, and more particularly to a system of an expandable three-dimension (3D) biodegradable and biocompatible polymer/nanomaterial scaffold and applications of the same.

BACKGROUND

The background description provided herein is for the purpose of generally presenting the context of the present disclosure. The subject matter discussed in the background of the invention section should not be assumed to be prior art merely as a result of its mention in the background of the invention section. Similarly, a problem mentioned in the background of the invention section or associated with the subject matter of the background of the invention section should not be assumed to have been previously recognized in the prior art. The subject matter in the background of the invention section merely represents different approaches, which in and of themselves may also be inventions. Work of the presently named inventors, to the extent it is described in the background of the invention section, as well as aspects of the description that may not otherwise qualify as prior art at the time of filing, are neither expressly nor impliedly admitted as prior art against the present disclosure.

In the complex bone fracture, bone trauma and some bone diseases, reconstruction of bone defects is required, and fillers are introduced for this purpose. Nowadays, the most common use filler being used to reconstruct the bone defects is the autograft. However, the use of autografts is limited by the availably and complex grafting procedure, and may combine with new fractures, more pain and longer surgery time.

Therefore, a heretofore unaddressed need exists in the art to address the aforementioned deficiencies and inadequacies.

SUMMARY

One of the objectives of this disclosure is to provide an expandable scaffold formed by a composite material that may be applied in a liquid, such as water or bodily fluid of a living subject, and uptake the liquid and expand to an expansion volume. The expandable scaffold may be introduced into certain locations of the living subject, such as a bone defect or a tissue defect, or may be introduced within or around an implantable device that is then disposed into the living subject.

In one aspect, the disclosure relates to an expandable scaffold. In one embodiment, the expandable scaffold includes a three-dimensional (3D) porous structure comprising a composite material composed by a first material and a second material. The 3D porous structure has a tunable expansion capacity. When applied in a liquid, the 3D porous structure is configured to uptake the liquid and expand from an original volume to an expansion volume up to 1000 times of the original volume.

In one embodiment, the 3D porous structure is formed by a plurality of layers of the composite material, and the layers of the composite material are arranged in accordance with a shape and a size of the expansion volume.

In one embodiment, the liquid is water or bodily fluid of a living subject.

In one embodiment, the 3D porous structure is disposed in a bone defect or a tissue defect of the living subject, and is configured to uptake bodily fluid of the living subject and expand to self-fit in the bone defect or the tissue defect.

In one embodiment, the expandable scaffold is disposed inside or around an implantable carrier, and the implantable carrier is disposed at a location within the living subject.

In one embodiment, the 3D porous structure is formed by injecting the composite material into a bone defect or a tissue defect of the living subject using an application device, such that the injected composite material uptakes bodily fluid of the living subject and expand to self-fit in the bone defect or the tissue defect. In one embodiment, the application device is a syringe.

In one embodiment, the expandable scaffold is loaded with a plurality of cells, drugs, antibiotics, growth factors or proteins.

In one embodiment, the first material includes one or more biocompatible and biodegradable polymers, and the second material is selected from a group consisting of hydroxyapatite, apatite, bone particles, calcium phosphate family or particles of multiple phases, calcium sulfate family or particles of multiple phases, graphitic materials, graphene, carbon nanotubes, carbon spheres, gold, silver nanomaterials, magnesium, zinc, or a combination thereof.

In one embodiment, the first material is polyurethane, and the second material is nanosized hydroxyapatite (nHA).

In one embodiment, the expandable scaffold is configured to be exposed to a gas plasma or corona discharge process to induce surface charges of positive, neutral or negative polarity.

In one embodiment, the expandable scaffold is configured to be exposed to a plasma polymerization coating process to introduce a surface coating on an external surface and an internal surface of the 3D porous structure, or to modify a surface charge of the expandable scaffold.

In one embodiment, a thickness of the surface coating ranges from 0.001 nm to 10 cm.

In one embodiment, the surface coating is formed by a biocompatible and biodegradable polymer material, comprising: (poly($\alpha$-esters), polyglycolide, polylactide, poly(L-lactic acid)(PLLA), poly(D-lactic acid)(PDLA), poly(D,L-lactic acid)(PDLLA), poly(lactide-co-glycolide), polyhydroxyalkanoates, poly(3-hydroxybutyrate), PHBV, Polycaprolactone (PCL), Poly(propylene fumarate)(PPF), polyanhydrides, polyacetals, poly(ortho esters), polycarbonates, poly(trimethylene carbonate)(PTMC), poly(desaminotyrosyltyrosine alkyl ester carbonates)(PDTEs), polyurethanes, polyphosphazenes, (poly[bis(trifluoroethoxy) phosphazene], polyphosphoesters, poly(ester ether)s, polydioxanone (PDO), poly($\beta$-amino esters)(PBAEs), poly (anhydride ester)s, poly(ester urethane)s, urethanes, polyurethanes, poly(ethylene glycol)(PEG), poly(propylene glycol)(PPG), triblock pluronic ([PEG]n-[PPG]m-[PEG]n), pluronic, PEG diacrylate (PEGDA), PEG dimethacrylate (PEGDMA), collagen, elastin, elastin-like polypeptides (ELPs), aAlbumin, fibrin, natural poly(amino acids), poly ($\gamma$-glutamic acid), poly(L-lysine), synthetic poly(amino acids), poly(L-glutamic acid), poly(aspartic acid), poly(aspartic acid)(PAA), polysaccharides, hyaluronic acid (HA), chondroitin sulfate (CS), polycaprolactone (PCL), chitin, chitosan, alginate, dextran, collagen, agarose, mannan or inulin.

In one embodiment, the expandable scaffold is designed to have a non-uniform density and packing density.

In one embodiment, the 3D porous structure has a porosity ranging from 1% to 99%.

In one embodiment, the expandable scaffold is designed to have a liquid uptake property ranging from 0 to 50000 times weight of the expandable scaffold.

In one embodiment, a composition weight ratio of the first material to the second material ranges from 0.01% to 99.99%.

In one embodiment, construction of the expandable scaffold is done by 3D bio-printing and hybrid printing and deposition technology by layer-by-layer deposition.

Another aspect of the disclosure relates to a bone regeneration system, which includes the expandable scaffold as discussed above. In one embodiment, the expandable scaffold is configured to be disposed at a location within a living subject in which bone formation and regeneration is required, wherein the second material includes bone particles, and the 3D porous structure of the expandable scaffold is configured to uptake bodily fluid of the living subject and expand at the location within the living subject.

In one embodiment, the expandable scaffold is disposed in a bone defect of the living subject, and the 3D porous structure of the expandable scaffold is configured to uptake bodily fluid of the living subject and expand to self-fit in the bone defect.

In one embodiment, the expandable scaffold is disposed inside or around an implantable carrier, and the implantable carrier is disposed at the location within the living subject.

In one embodiment, the bone regeneration system further includes an application device configured to inject the expandable scaffold into the location within the living subject, such that the injected composite material uptakes bodily fluid of the living subject and expand to form the expandable scaffold. In one embodiment, the application device is a syringe.

A further aspect of the disclosure relates to a soft tissue regeneration system, which includes the expandable scaffold as discussed above. In one embodiment, the expandable scaffold is configured to be disposed within a tissue defect of a living subject in which soft tissue formation and regeneration is required, wherein the 3D porous structure of the expandable scaffold is configured to uptake bodily fluid of the living subject and expand to self-fit in the tissue defect.

In one embodiment, the soft tissue of the living subject includes muscle, skin, nerve, blood arteries and vessels of the living subject.

Yet a further aspect of the disclosure relates to a bleed stopping device, which includes the expandable scaffold as discussed above. In one embodiment, the expandable scaffold is configured to be disposed at a location of a living subject in which bleeding occurs, wherein the 3D porous structure of the expandable scaffold is configured to uptake blood of the living subject and expand to stop the bleeding.

In another aspect, the disclosure relates to a method for fabricating an expandable scaffold. In one embodiment, the method includes: providing a three-dimensional (3D) porous structure comprising a composite material composed by a first material and a second material, forming the expandable scaffold, wherein the 3D porous structure has a tunable expansion capacity, and when applied in a liquid, is configured to uptake the liquid and expand from an original volume to an expansion volume up to 10000 times of the original volume.

In one embodiment, the method also includes: forming the 3D porous structure by a plurality of layers of the composite material; and arranging the layers of the composite material in accordance with a shape and a size of the expansion volume.

In one embodiment, the method also includes: disposing the 3D porous structure in a bone defect or a tissue defect of a living subject, such that the 3D porous structure uptakes bodily fluid of the living subject and expand to fit in the bone defect or the tissue defect.

In one embodiment, the method also includes: disposing the expandable scaffold inside or around an implantable carrier; and disposing the implantable carrier at a location within a living subject.

In one embodiment, the method also includes: injecting the composite material into a bone defect or a tissue defect of the living subject using an application device to form the expandable scaffold, such that the injected composite material uptakes bodily fluid of the living subject and expand to self-fit in the bone defect or the tissue defect.

In one embodiment, the expandable scaffold is loaded with a plurality of cells, drugs, antibiotics, growth factors or proteins.

In one embodiment, the first material includes one or more biocompatible and biodegradable polymers, and the second material is selected from a group consisting of hydroxyapatite, apatite, bone particles, calcium phosphate family or particles of multiple phases, calcium sulfate family or particles of multiple phases, graphitic materials, graphene, carbon nanotubes, carbon spheres, gold, silver nanomaterials, magnesium, zinc, or a combination thereof.

In one embodiment, the first material is polyurethane, and the second material is nanosized hydroxyapatite (nHA).

In one embodiment, the method further includes: exposing the expandable scaffold to a gas plasma or corona discharge process to induce surface charges of positive, neutral or negative polarity.

In one embodiment, the method further includes: exposing the expandable scaffold to a plasma polymerization coating process to introduce a surface coating on an external surface and an internal surface of the 3D porous structure, or to modify a surface charge of the expandable scaffold.

In one embodiment, a thickness of the surface coating ranges from 0.001 nm to 1 cm. In one embodiment, the surface coating is formed by a biocompatible and biodegradable polymer material comprising: (poly(α-esters), polyglycolide, polylactide, poly(L-lactic acid)(PLLA), poly (D-lactic acid)(PDLA), poly(D,L-lactic acid)(PDLLA), poly (lactide-co-glycolide), polyhydroxyalkanoates, poly(3-hydroxybutyrate), PHBV, Polycaprolactone (PCL), Poly (propylene fumarate)(PPF), polyanhydrides, polyacetals, poly(ortho esters), polycarbonates, poly(trimethylene carbonate)(PTMC), poly(desaminotyrosyltyrosine alkyl ester carbonates)(PDTEs), polyurethanes, polyphosphazenes, (poly[bis(trifluoroethoxy)phosphazene], polyphosphoesters, poly(ester ether)s, polydioxanone (PDO), poly(β-amino esters)(PBAEs), poly(anhydride ester)s, poly(ester urethane)s, urethanes, polyurethanes, poly(ethylene glycol) (PEG), poly(propylene glycol)(PPG), triblock pluronic ([PEG]n-[PPG]m-[PEG]n), pluronic, PEG diacrylate (PEGDA), PEG dimethacrylate (PEGDMA), collagen, elastin, elastin-like polypeptides (ELPs), aAlbumin, fibrin, natural poly(amino acids), poly(γ-glutamic acid), poly(L-lysine), synthetic poly(amino acids), poly(L-glutamic acid), poly (aspartic acid), poly(aspartic acid)(PAA), polysaccharides, hyaluronic acid (HA), chondroitin sulfate (CS), polycaprolactone (PCL), chitin, chitosan, alginate, dextran, collagen, agarose, mannan or inulin.

In one embodiment, the expandable scaffold is designed to have a non-uniform density and packing density.

In one embodiment, the 3D porous structure has a porosity ranging from 1% to 99%.

In one embodiment, the expandable scaffold is designed to have a liquid uptake property ranging from 0 to 50000 times weight of the expandable scaffold.

In one embodiment, a composition weight ratio of the first material to the second material ranges from 0.01% to 99.99%.

In one embodiment, construction of the expandable scaffold is done by 3D bio-printing and hybrid printing technology by layer-by-layer deposition.

These and other aspects of the invention will become apparent from the following description of the preferred embodiment taken in conjunction with the following drawings, although variations and modifications therein may be affected without departing from the spirit and scope of the novel concepts of the invention.

BRIEF DESCRIPTION OF THE DRAWINGS

The accompanying drawings illustrate one or more embodiments of the invention and, together with the written description, serve to explain the principles of the invention. Wherever possible, the same reference numbers are used throughout the drawings to refer to the same or like elements of an embodiment.

DETAILED DESCRIPTION

Figure 1B:
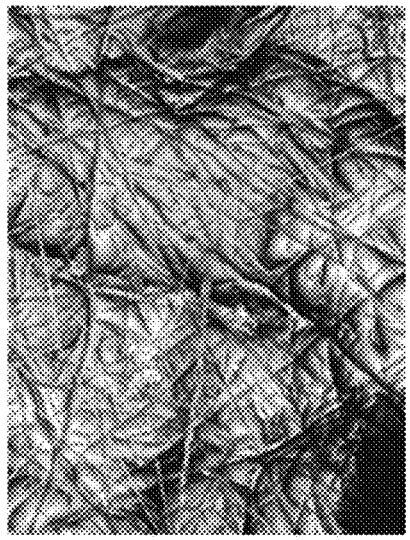
FIGS. 1A and 1B show images of an expandable scaffold in different spots of its 3D porous structure according to certain embodiments of the disclosure.

The disclosure will now be described more fully hereinafter with reference to the accompanying drawings, in which exemplary embodiments of the disclosure are shown. This invention may, however, be embodied in many different forms and should not be construed as limited to the embodiments set forth herein. Rather, these embodiments are provided so that this disclosure will be thorough and complete, and will fully convey the scope of the disclosure to those skilled in the art. Like reference numerals refer to like elements throughout.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks. The use of highlighting and/or capital letters has no influence on the scope and meaning of a term; the scope and meaning of a term are the same, in the same context, whether or not it is highlighted and/or in capital letters. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only and in no way limits the scope and meaning of the disclosure or of any exemplified term. Likewise, the disclosure is not limited to various embodiments given in this specification.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third, etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below can be termed a second element, component, region, layer or section without departing from the teachings of the disclosure.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" to another feature may have portions that overlap or underlie the adjacent feature.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising", or "includes" and/or "including" or "has" and/or "having" when used in this specification specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top", may be used herein to describe one element's relationship to another element as illustrated in the figures. It will be understood that relative terms are intended to encompass different orientations of the device in addition to the orientation shown in the figures. For example, if the device in one of the figures is turned over, elements described as being on the "lower" side of other elements would then be oriented on the "upper" sides of the other elements. The exemplary term "lower" can, therefore, encompass both an orientation of lower and upper, depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used herein, the terms "comprise" or "comprising", "include" or "including", "carry" or "carrying", "has/have" or "having", "contain" or "containing", "involve" or "involving" and the like are to be understood to be open-ended, i.e., to mean including but not limited to.

As used herein, the phrase "at least one of A, B, and C" should be construed to mean a logical (A or B or C), using a non-exclusive logical OR. It should be understood that one or more steps within a method may be executed in different order (or concurrently) without altering the principles of the disclosure.

Typically, terms such as "about," "approximately," "generally," "substantially," and the like unless otherwise indicated mean within 20 percent, preferably within 10 percent, preferably within 5 percent, and even more preferably within 3 percent of a given value or range. Numerical quantities given herein are approximate, meaning that the term "about," "approximately," "generally," or "substantially" can be inferred if not expressly stated.

Typically, "nanoscopic-scale," "nanoscopic," "nanometer-scale," "nanoscale," the "nano-" prefix, and the like refers to elements or articles having widths or diameters of less than about 1 µm, preferably less than about 100 nm in some cases. Specified widths can be smallest width (i.e. a width as specified where, at that location, the article can have a larger width in a different dimension), or largest width (i.e., where, at that location, the article's width is no wider than as specified, but can have a length that is greater), unless pointed out otherwise.

Embodiments of the invention are illustrated in detail hereinafter with reference to accompanying drawings. It should be understood that specific embodiments described herein are merely intended to explain the invention, but not intended to limit the invention. In accordance with the purposes of this invention, as embodied and broadly described herein, this invention, in certain aspects, relates to three-dimension (3D) biodegradable, biocompatible polymer/nanomaterial expandable scaffolds, fabricating methods thereof, and applications of the same.

As discussed above, the use of autografts as fillers to reconstruct the bone defects is limited. Tissue engineering providing an alternative solution by utilizing biocompatible materials to make a bone scaffold, mimicking the bone structure and component of organic (soft) and inorganic (hard) components. Biocompatible Polymers have been widely used for fabrication of synthetic bone scaffolds, and the biodegradable polyurethane promote the growth of cells and tissues in vitro and in vivo. Hydroxyapatite (HA) is a neutral inorganic component of bone, which is known for its unique biological properties, such as biocompatibility, bioactivity, and osteointegration. Thus, the HA has become attractive material for synthetic bone graft. Further study shows using nanosized HA (nHA), microsized HA or macrosized HA supports cellular adhesion and proliferation.

A composite material of polyurethane and nHA (nanosized HA) is shown to be cytocompatible, and provide suitable environmental cell adhesion, proliferation, and osteogenic differentiation in vitro. Furthermore, a composition of 80% polyurethane and 20% nHA shows a linear increase in proliferation of MC3T3-E1 cells in vitro. The ratio can be varied from 0.01 wt. % to the value that would result in the disintegration of the composite and its inability to maintain its structure (usually over 50 wt. %).

Natural bone particles (decellularized or demineralized bone matrix) of various sources (bovine, human/cadaveric, porcine, etc.) could be utilized with various biodegradable/ biocompatible polymers (polyurethanes, etc) and nHA for making synthetic bone scaffolds.

In some critical bone size, shape and non-uniformly shaped bone defect, it is not easy to insert the bone grafts inside the bone cavity, and scaffold need to be adjusted to the size and shape of cavity, special tools need to be used for that purpose, which increase the surgery duration and bone losses. Further, the available fabrication techniques of scaffolds restrict shaping the scaffold in proper way that can occupy the defect and be in contact with the tissue. Thus, developing a scaffold that can be easily implemented in the defect, minimizing the surgery invasion by using injection, or self-fitting scaffolds become attractive for researchers.

An injectable scaffold needs to meet a number of requirements. For example, bone osseointegration needs the scaffold to firmly fill the defect, and the scaffold has to be osteoconductive and porous to promote the new bone growth inside its structure. Further, the scaffold material should be biodegradable, as the scaffold material needs to degrade in the new bone growth process to allow new bone formation. Some of studies utilize the polycaprolactone (PCL) for the sell-fitting scaffold and injectable scaffold. However, the polycaprolactone has long degradation period for bone application, and it was suggested that a biomaterial with higher degradation rate is required.

Many studies introduce the shape memory effect to produce a self-fitting scaffolds, where the scaffold needs external stimulus such as heat to recover its original shape and structure from a compact structure, and to take the shape of the defect. However, the external stimuli add more complexity to surgery.

In certain aspects, the disclosure is to provide an expandable scaffold, which formed by a composite material in one or more layers forming a 3D porous structure. When the 3D porous structure is applied in a liquid, such as water or bodily fluid of a living subject, the 3D porous structure may uptake the liquid and expand to an expansion volume. The expandable scaffold may be introduced into certain locations of the living subject, such as a bone defect or a tissue defect, or may be introduced within or around an implantable device that is then disposed into the living subject. For example, the implantable device may be an implant normally used in the medical practice such as a carrier, a spine cage or similar device, or a bone implant that is metallic or non-metallic. The expansion could take place due to the structural or morphological changes that take place within the bulk of the scaffold or other mechanisms that include the body fluids uptake and swelling. The scaffold can increase in the volume from 0 to a volume that is equal with the volume that is required to be filled by the final structure of the scaffold. In certain embodiments, the scaffold for example could expand up to 10000 times or more or less of its original volume, depending upon the actual application. Based on the final architecture, the scaffold can be used for bone regeneration, but also for soft tissue regeneration (muscle, skin, nerve, blood arteries and vessels, etc).

In one embodiment, the 3D porous structure of the expandable scaffold includes a composite material composed by a first material (which is a soft material) and a second material (which is a hard material), or mixture of soft and hard materials. The 3D porous structure has a tunable expansion capacity. When applied in a liquid (such as water or bodily fluid of a living subject), the 3D porous structure is configured to uptake the liquid and expand from an original volume to an expansion volume up to 10000 times of the original volume. In one embodiment, the 3D porous structure is formed by a plurality of layers and mixtures of the composite material, and architecture and shape of the layers of the composite material are arranged in accordance with a shape and a size of the expansion volume. In one embodiment, the 3D porous structure is formed by controlled mixing, in a successive or simultaneous manner, of the components into a uniform composition. The mixture that is formed by the mixing of the components can be arranged into layers or various geometrical shapes. In one embodiment, the 3D porous structure is formed by the controlled mixing of the various materials in a simultaneous or in a certain order based on the desired characteristics of the scaffold. In one embodiment, construction of the expandable scaffold is done by selective solvent extraction and by controlled mixing of the components and followed by possible controlled removal of the solvent. In one embodiment, the scaffolds can also be mixed and printed into anatomically correct shapes that mimic the part of the bone that needs to be regenerated.

Figure 1A:
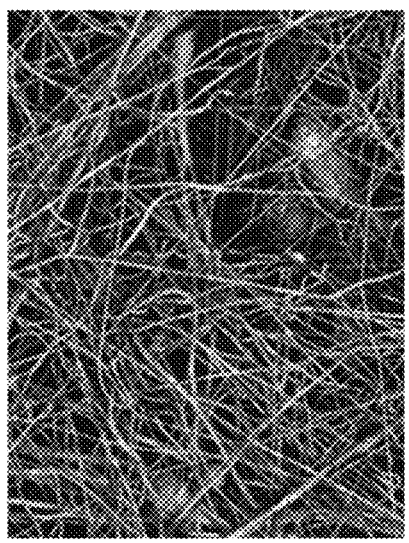

In certain embodiments, the expandable scaffold can take any complex shape during the application. FIGS. 1A and 1B show images of an expandable scaffold in different spots of its 3D porous structure according to certain embodiments of the disclosure. As shown in FIGS. 1A and 1B, the internal morphology of the expandable scaffold can be nano- or micro-fibers formed by the composite materials.

In one embodiment, the 3D porous structure of the expandable scaffold (or one or more of the 2D layers thereof) acts as the self-fitting bone or tissue filler, which can expand by swelling in the liquid or by transformation into its volume structure, in order to occupy the shape of defect or the volume to be filled and increase its shape dynamically as a function of time.

In one embodiment, the 3D porous structure is disposed alone in a bone defect or a tissue defect of the living subject. In this case, the scaffold would uptake bodily fluid of the living subject and expand to self-fit in the bone defect or the tissue defect. Alternatively, in another embodiment, the expandable scaffold can also be disposed inside or around an implantable carrier, and the implantable carrier is then disposed at a location within the living subject. For example, the scaffold can be applied inside of various rigid or non-rigid industry standard or customized implantable carriers or cages (which may be metallic, carbon or polymeric), and then the implant can be implanted into any part of the body such as craniomaxillofacial, extremities, spine, pelvis, etc. In a further embodiment, the application of the expandable scaffold can be done with an application device either in a solid or expanded state. For example, the 3D porous structure may be formed by injecting or placing the composite material into a bone defect or a tissue defect of the living subject using an application device, such that the injected composite material uptakes bodily fluid of the living subject and expand to self-fit in the bone defect or the tissue defect. In one embodiment, the application device may be a syringe, or may be a medical device that allows the precise delivery and accurate positioning of the scaffold into the desired bone defect and location. In one embodiment, the scaffold can also be placed during surgery by exposing the bone void and by tightly placing the scaffold into the desired position.

In certain embodiments, the scaffold can be rigid with no volume expansion, or can expand multiple times its original volume through liquid (water, blood, body fluids, etc) interactions and uptake. In another application, the scaffold can be applied as an injectable scaffold, where a sample of known volume can be injected or introduced through an applicator such as syringe, with openings of various diameters.

In one embodiment, the expandable scaffold, which is formed by a composite material composed of the first material (which is a soft material) and the second material (which is a hard material), is designed to mimic the natural bone of soft and elastic component (collagen) and hard mineral component. The porosity of the scaffold can be varied between basically 0 to 99.999999% and its water uptake properties can be varied from 0 to 50000 times the scaffolds' weight. For example, the 3D porous structure may be designed to have a porosity ranging from 1% to 99%, and a liquid uptake property ranging from 0 to 50000 times weight of the expandable scaffold.

The composite material forming the expandable scaffold includes multiple major types of materials. The first material is a soft material, such as one or multiple polymers. The second material is a hard material, which can be organic or inorganic, such as one or more components of human/animal or synthesized origin. The second material may include, without being limited thereto, the following materials and their derivatives: hydroxyapatite, apatites, bone particles (processed, decellularized or demineralized, or unprocessed), calcium phosphate family or particles of various phases (b-Tricalcium phosphate, or the family of such materials, etc), calcium sulfate family or particles of various phases, graphitic nano-, micro- or macro-sized materials such as graphene, carbon nanotubes, carbon spheres, gold, silver nanomaterials, magnesium, zinc, or other metals/metal oxides in both nano, micro or bulk sizes, etc. The bone particles could be human, bovine, porcine or other animal origins. All these materials can be sized at the nano, micro size or bulk, and they can be mixed in various dimensional ranges. The ratio between the soft material (such as polymers) and the hard material (such as various organic and inorganic systems) may be varied from 0.001 to 99.99 wt. %. For example, a composition weight ratio of the first material to the second material ranges from 0.01% to 99.99%. The polymers used as the first material are biocompatible and biodegradable, with a degradation rate from minutes to multiple years. Examples of the natural or synthetic biocompatible and/or biodegradable polymers may include, without being limited thereto, (Poly($\alpha$-esters), Polyglycolide, Polylactide, poly(L-lactic acid)(PLLA), poly(D-lactic acid)(PDLA), poly(D,L-lactic acid)(PDLLA), Poly(lactide-co-glycolide), Polyhydroxyalkanoates, poly(3-hydroxybutyrate), PHBV, Polycaprolactone (PCL), Poly (propylene fumarate)(PPF), Polyanhydrides, Polyacetals, Poly(ortho esters), Polycarbonates, poly(trimethylene carbonate)(PTMC), poly(desaminotyrosyltyrosine alkyl ester carbonates)(PDTEs), Polyphosphazenes, (poly[bis(trifluoroethoxy)phosphazene], Polyphosphoesters, Poly(ester ether)s, polydioxanone (PDO), poly($\beta$-amino esters) (PBAEs), poly(anhydride ester)s, Poly(ester urethane)s, urethanes (ether, or polyether, aliphatic or organic), polyurethanes, poly(ethylene glycol)(PEG), poly(propylene glycol) (PPG), triblock Pluronic ([PEG]n-[PPG]m-[PEG]n), Pluronic, PEG diacrylate (PEGDA), PEG dimethacrylate (PEGDMA), Collagen (types I, II, III, and IV), elastin, elastin-like polypeptides (ELPs), Albumin, fibrin, natural poly(amino acids), poly($\gamma$-glutamic acid), poly(L-lysine), Synthetic Poly(amino acids), poly(L-glutamic acid), poly (aspartic acid), Poly(aspartic acid)(PAA), Polysaccharides, Hyaluronic acid, chondroitin sulfate (CS), Polycaprolactone (PCL), Chitin, Chitosan, Alginate, dextran, collagen, agarose, mannan or inulin.

In one embodiment, the first material is a biocompatible/biodegradable polymer such as polyurethane or ether-based hydrophilic urethanes (or a mixture of such polymers with various degradable rates), and the second material is nano-sized/macrosized hydroxyapatite (nHA).

In one embodiment, the polymer/hydroxyapatite composite is integrated with bone derived particles (such as decellularized, demineralized, etc) or calcium phosphate family of materials or calcium sulfate family of particulate materials, or combination of these materials. Furthermore a sacrificial material (salt, sugar, or a fast degrading/dissolving polymer or material) can be integrate in this composite and upon removal into a water or solvent bath, would generate desired porosity with interconnected pores.

In one embodiment, the expandable scaffold is configured to be exposed to a gas (nitrogen, oxygen, helium, argon, or mixtures, etc) plasma or corona discharge process to induce surface charges of positive, neutral or negative polarity or mixtures. The process can be used to increase the roughness of the surface morphology and introduce atoms and functional groups onto the surface.

In one embodiment, the expandable scaffold is configured to be exposed to a plasma polymerization coating process to introduce a surface coating on an external surface and an internal surface of the 3D porous structure, or to modify a surface charge of the expandable scaffold. For example, the internal and external surfaces of the 3D porous structure and/or a bulk of the 3D porous structure of the expandable scaffold may be coated with nanostructural materials by using plasma polymerizations coating. In one embodiment, a thickness of the surface coating ranges from 0.001 nm to 1 cm. Different materials can be used modify the internal/external surface coating of the expandable scaffold, such as a natural or synthetic biocompatible and/or biodegradable (fast or slowly) polymer, with a degradation rate from minutes to multiple years. Examples of the biocompatible and biodegradable polymer material for the surface coating may include, without being limited thereto, HydroMed™ family (D1, D2, D3, D4, D6, D640, D7), Pellethane® thermoplastic polyurethanes, Tecobax™ thermoplastic polyurethane (TPU), Tecoflex™ aliphatic polyether-based thermoplastic polyurethanes (TPUs), Tecophilic™ thermoplastic polyurethanes (TPUs), Tecoplast™ thermoplastic polyurethanes (TPUs), Tecothane™ aromatic polyether-based thermoplastic, (poly($\alpha$-esters), polyglycolide, polylactide, poly(L-lactic acid)(PLLA), poly(D-lactic acid) (PDLA), poly(D,L-lactic acid)(PDLLA), poly(lactide-co-glycolide), polyhydroxyalkanoates, poly(3-hydroxybutyrate), PHBV, Polycaprolactone (PCL), Poly(propylene fumarate)(PPF), polyanhydrides, polyacetals, poly(ortho esters), polycarbonates, poly(trimethylene carbonate) (PTMC), poly(desaminotyrosyltyrosine alkyl ester carbonates)(PDTEs), polyurethanes, polyphosphazenes, (poly[bis (trifluoroethoxy)phosphazene], polyphosphoesters, poly (ester ether)s, polydioxanone (PDO), poly($\beta$-amino esters) (PBAEs), poly(anhydride ester)s, poly(ester urethane)s, urethanes, polyurethanes, poly(ethylene glycol)(PEG), poly (propylene glycol)(PPG), triblock pluronic ([PEG]n-[PPG] m-[PEG]n), pluronic, PEG diacrylate (PEGDA), PEG dimethacrylate (PEGDMA), collagen, elastin, elastin-like polypeptides (ELPs), aAlbumin, fibrin, natural poly(amino acids), poly($\gamma$-glutamic acid), poly(L-lysine), synthetic poly (amino acids), poly(L-glutamic acid), poly(aspartic acid), poly(aspartic acid)(PAA), polysaccharides, hyaluronic acid (HA), chondroitin sulfate (CS), polycaprolactone (PCL), chitin, chitosan, alginate, dextran, collagen, agarose, mannan or inulin. In one embodiment, some of the polymers can be composed of groups such as PEG, PPO, PBO, that would help with water uptake. The polymer can be hydrogel.

In certain embodiments, the expandable scaffold can be designed to have a uniform or non-uniform density and packing density. For example, the density at the edges of the expandable scaffold can be higher or lower compared to the interior thereof.

In certain embodiments, the construction of the scaffold can be done by using solvent extraction, mixing of components, selective materials removal approaches, high air pressure spraying, 3D bio-printing and hybrid printing/deposition technology such as layer-by-layer deposition or additive manufacturing. In one embodiment, the construction of the expandable scaffold can be done by placing the wet scaffold into a water bath, dried, and shaped to the required size or shape by cutting or molding into the desired shapes and sizes.

In one embodiment, the expandable scaffold is loaded with a plurality of cells, drugs, antibiotics, growth factors or proteins that are pertinent to tissue formation and controlling and removing infections and diseases. For example, the expandable scaffold can be delivered in vivo with one or multiple bio-active systems, including, without being limited thereto:

Antibiotics to fight infections involving both gram positive and gram negative bacteria: that include but are not limited to Cefazolin, Cefuroxime, Flucloxacillin and gentamicin, Ceftriaxone, Clindamycin, Vancomycin, ciprofloxacin, tigecycline, tobramycin, Piperacillin, tazobactam, lovastatinetc. The loading ratios of the antibiotics could be varied from 0 to the maximum loading capacity. The antibiotic uptake can take place in the porosity of the scaffold or in the structure of the polymers used in the construction of the scaffold.

Phosphonate family of compounds.

Anti-cancer drugs (one or multiple) that include but are not limited to: Doxorubicin (Adriamycin), Mitotane, Cisplatin, Carboplatin, Etoposide (VP-16), Ifosfamide (Ifex), Cyclophosphamide (Cytoxan), Vincristine (Oncovin), Abitrexate (Methotrexate), Cosmegen (Dactinomycin), Doxorubicin Hydrochloride, Folex (Methotrexate), Folex PFS (Methotrexate), Methotrexate, Methotrexate LPF (Methotrexate), Mexate (Methotrexate), Mexate-AQ (Methotrexate), Xgeva (Denosumab), Vincristine, ifosfamide, doxorubicin, etoposide (VIDE), Vincristine, actinomycin and ifosfamide (VAI), Vincristine, actinomycin D (dactinomycin) and cyclophosphamide (VAC), Methotrexate (Maxtrex), Etoposide (Eposin, Etopophos, Vepesid), Ifosfamide (Mitoxana), Docetaxel (Taxotere), Gemcitabine (Gemzar), Carboplatin (Paraplatin), Irinotecan Campto), Temozolomide (Temodal), Topotecan (Hycamtin, Potactasol), paclitaxel, Granulocyte colony stimulating factor (G-CSF), 5-fluorouracil, Actinomycin D (dactinomycin, Cosmegen). The loading ratios of the drugs could be varied from 0 to the maximum loading capacity. The drug uptake can take place in the porosity of the scaffold or in the structure of the polymers used in the construction of the scaffold.

Osteoporosis treatment drugs such as: Fosamax, Zometa, estradiol, hydrochlorothiazide, Boniva, calcium/vitamin d, calcium carbonate, Alendronate, Forteo, Reclast, Prolia, Caltrate, Caltrate 600+D, Evista, risedronate, Citracal+D, Atelvia, ibandronate, Premarin, raloxifene, Actonel, calcitonin, teriparatide, zoledronic acid, denosumab, A variety of growth factors (one or multiple) that include, but are not limited to: platelet-rich plasma (PRP), platelet-derived growth factor (PDGF), vascular endothelial growth factor (VEGF), fibroblast growth factor (FGF), OP-1/BMP-7, OP-2/BMP-8, BMP-Sb, BMP-5, BMP-6/Vgr-1, GDF-5/CDMP-1/BMP-14, GDF-6/CDMP-2/BMP-13, GDF-7/BMP-12, BMP-9/GDF-2, BMP-10, Dorsalin-1, BMP-15, Vg-1 (Xenopus), GDF-1, GDFs GDF-3/Vgr-2, GDF-8, GDF-9, GDF-11/BMP-11, GDF-12, GDF-14, IGF-I, IGF-II, TGF-p, TGF&, Basic FGF, Acidic FGF, PDGF, BMP-2, BMP-3, BMP-4, BMP-5, BMP-6, BMP-7, BMP-12, BMP-13, DNA, RNA, plasmids, proteins, or similar growth factors that have as function the acceleration of tissue formation, new blood vessel generation or activation of various biological functions, etc.

A variety of cells, such as osteoblasts, osteoclasts, stem cells (of various origins such as human, or animal, pre or post differentiation), mesenchymal stem cells, osteocytes, etc.

In certain embodiments, the expandable scaffold may be used for bone regeneration based on the final architecture. For example, in one embodiment, a bone regeneration system may include the expandable scaffold, which is used to be disposed at a location within a living subject in which bone formation and regeneration is required. In one embodiment, the hard material of the expandable scaffold being used in the bone regeneration system may include bone particles, and the 3D porous structure of the expandable scaffold is configured to uptake bodily fluid, cells, and/or growth factors of the living subject and expand at the location within the living subject. For example, the expandable scaffold may be disposed in a bone defect of the living subject. In this case, the 3D porous structure of the expandable scaffold may uptake bodily fluid of the living subject and expand to self-fit in the bone defect. Alternatively, the expandable scaffold may be disposed inside or around an implantable carrier, and the implantable carrier is disposed at the location within the living subject. Alternatively, an application device (such as a syringe) may be used to inject or place the expandable scaffold into the location within the living subject, such that the injected composite material uptakes bodily fluid of the living subject and expand to form the expandable scaffold.

In certain embodiments, the expandable scaffold may be used for soft tissue regeneration (muscle, skin, nerve, blood arteries and vessels, etc). For example, in one embodiment, a soft tissue regeneration system may include the expandable scaffold, which is disposed within a tissue defect of a living subject in which soft tissue formation and regeneration is required. The 3D porous structure of the expandable scaffold may uptake bodily fluid of the living subject and expand to self-fit in the tissue defect.

In one embodiment, the expandable scaffold alone or along with one or multiple combinations of cells, drugs/antibiotics, growth factors/proteins can be placed into a bone defects of various shapes or sizes, or in bone defects that have 4, 3, 2, or 1 bone walls/surfaces. In another embodiment, the expandable scaffold alone or along with one or multiple combinations of cells, drugs/antibiotics, growth factors/proteins can be placed next to a bone wall in order to increase the amount of bone formed along that particular bone surface. For example, the expandable scaffold can be placed around a medically used implant, nails, screws, devices that could be metallic or non-metallic and used in joint replacement, bone fixation, bone fracture stabilization, and other medically relevant applications in which bone formation and regeneration is required. In another embodiment, the expandable scaffold may be included into medically used devices such as cages that are placed into bone structures. The scaffold possibly carrying bio-active molecules, proteins, (growth factors, ex BMPs) and/or drugs (antibiotics, or various drugs as seen above) can be included into the cages and expand as the cages are introduced into the bone structures (dental, spine, pelvis, long bone, etc) and the scaffold can expand along with cage expansion.

In one embodiment, the expandable scaffold may be used for dental applications, where the scaffold is placed into an extraction socket, around the tooth root, around the implant surface and intertwined with the implant structure and morphology, large segmental bone defect, alone or in the presence of antibiotics, drugs, cells or growth factors.

Figure 2:
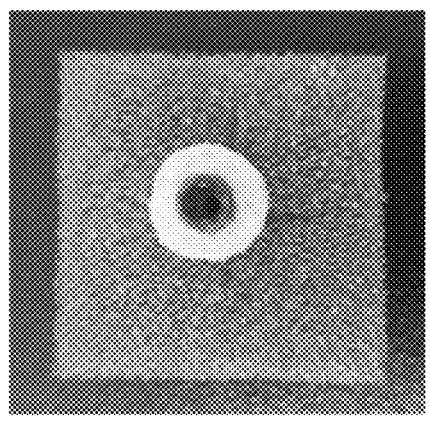
FIG. 2 shows images of a combination of an expandable scaffold with an implant in different viewing angles according to one embodiment of the disclosure.
Figure 2:
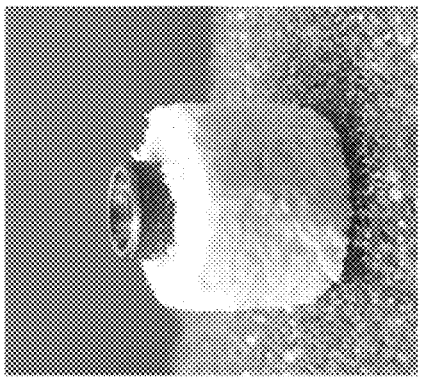
Figure 2:
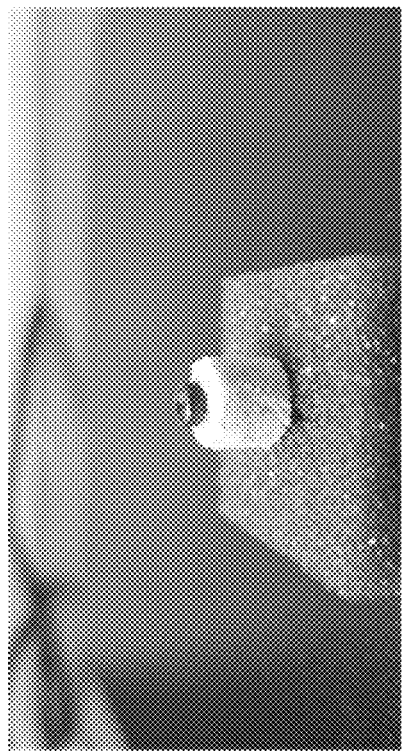

In one embodiment, the expandable scaffold is placed around a dental implant either during the scaffold manufacturing or the implant is placed into the scaffold after the scaffold it is manufactured. For example, FIG. 2 shows images of a combination of an expandable scaffold with an implant in different viewing angles according to one embodiment of the disclosure. As shown in FIG. 2, the expandable scaffold is disposed around the implant. The combination of the two systems can be implanted together in order to provide mechanical support and also provide a medium of bone regeneration and integration of the implant. The combination scaffold/implant along with one or multiple combinations of cells, drugs/antibiotics, growth factors/proteins can be implanted together. The thickness of the scaffold around the implant surface can vary from 0.001 mm to 10 cm or the actual value that is needed for a particular application. The scaffold can also have an anatomically correct shape that is required to build a complex bone defect, and such a defect can be obtained through 3D CT scanning.

In one embodiment, the scaffold with one or multiple combinations of cells, drugs/antibiotics, growth factors/proteins can be used for the partial or complete craniomaxillofacial bone regeneration, such as but not limited to regenerate bone gaps or the entire structure in the mandible, skull, nasal bone and septum, maxilla, zygomatico-maxillary structure, maxilla, etc. Such combination can be used for the partial or complete regeneration of long bones, such as but not limited to tibia, femur, humerus, ulma, radius, fibula, but also patella, phalanges, metatarsals, metacarpals, sacrum, pelvic structure, vertebrae, ribs, spinal column, spine, cervical vertebrae, etc.

In one embodiment, the scaffold with one or multiple combinations of cells, drugs/antibiotics, growth factors/proteins can be placed can be used for spine tissue regeneration alone or inside a cage (metal, carbon, polymer, etc) of another devices of various dimensions that are normally used for such applications.

In one embodiment, the scaffold with one or multiple combinations of cells, drugs/antibiotics, growth factors/proteins can be used to fill up the space and ensure bone regeneration between the surface of an implant and the bone surface. This volume can be of various shapes and dimensions in various parts of the body.

In one embodiment, the expandable scaffold may be used as a bleed stopping device, which may be disposed at a location of a living subject in which bleeding occurs. The 3D porous structure of the expandable scaffold may uptake blood of the living subject and expand to stop the bleeding. Based on the degree of expansion or fluid uptake, the expandable scaffold may expand up to 1000 times of its original size, and may uptake/store fluid within range of (0-10000) of its original weight. The expandable scaffold may be used to treat internal/or external bleeding. Further, the expandable scaffold may also prevent/fight/treat skin/or tissue inflammation.

In one embodiment, the expandable scaffold (or one or more 2D layers thereof) with one or multiple combinations of cells, drugs/antibiotics, growth factors/proteins may work as skin graft/scaffold. The scaffold may be formed from different layers, such as 1-10000 layers. Each layer can be design to have it unique fluid uptake, and the thickness of each layer may range from 0.001 nm to 10 cm. In one embodiment, the device can be directly loaded/coated the injury site through high air pressure spraying.

With the recent rapid development in bioengineering and biomaterial sciences, the expandable scaffold as described in the embodiments of the disclosure provides a promising solution for bone fracture therapy. In case of critical size bone defects or bones that are located in critical position, doing surgery becomes very hard and minimum surgical intervention is needed. Thus, the expandable scaffold has the self-fitting and/or injectable feature, which may occupy the irregular shape of a bone defect by injection through small hole or have small scaffold that can expand to take the shape of defect. The expandable scaffold is biocompatible, biodegradable and porous in order to improve the healing process of bone while promoting neovascularization and allowing the cells proliferate and expand in its bulk and surface. The expandable scaffold is also provided with tunable expansion capacity based on the particular applications and possibly injectable scaffold that can expand by swelling at exposure to bodily fluids or other liquids to take the non-uniform shape of bone defect, or be injected through small hole and fill the defect shape. In certain embodiments, the scaffold may match the expansion volume of a medical device that is introduced thereto. The scaffold may be introduced alone in the non-uniform bone defect, or inside a commonly used industry standard device or around a device (implant, etc.) that is desired to be anchored into the bone structure. The scaffold design is such that mimics the natural architecture of bone, with nano-macro hard/soft components that support osteogenesis.

In another aspect, the disclosure relates to a method for fabricating an expandable scaffold. In one embodiment, the method includes: providing the 3D porous structure comprising a composite material composed by a first material and a second material, forming the expandable scaffold, where the 3D porous structure has a tunable expansion capacity, and when applied in a liquid, is configured to uptake the liquid and expand from an original volume to an expansion volume up to 1000 times of the original volume.

In one embodiment, the method also includes: forming the 3D porous structure by a plurality of layers of the composite material; and arranging the layers of the composite material in accordance with a shape and a size of the expansion volume.

In one embodiment, the method includes: forming a 3D porous structure by controlled mixing of a variety of composition materials and arranging them into the shape that is desired for the regeneration application and then by solvent extraction obtain the desired porosity. The scaffold can then be introduced a liquid and then dried, before being shaped into the desired shape and size.

In one embodiment, the method also includes: disposing the 3D porous structure in a bone defect or a tissue defect of a living subject, such that the 3D porous structure uptakes bodily fluid of the living subject and expand to fit in the bone defect or the tissue defect.

In one embodiment, the method also includes: disposing the expandable scaffold inside or around an implantable carrier; and disposing the implantable carrier at a location within a living subject.

In one embodiment, the method also includes: injecting or placing the composite material into a bone defect or a tissue defect of the living subject using an application device to form the expandable scaffold, such that the injected composite material uptakes bodily fluid of the living subject and expand to self-fit in the bone defect or the tissue defect.

In one embodiment, the method further includes: exposing the expandable scaffold to a gas plasma or corona discharge process to induce surface charges of positive, neutral or negative polarity.

In one embodiment, the method further includes: exposing the expandable scaffold to a plasma polymerization coating process to introduce a surface coating on an external surface and an internal surface of the 3D porous structure, or to modify a surface charge of the expandable scaffold.

These and other aspects of the present invention are further described in the following section. Without intending to limit the scope of the invention, further exemplary implementations of the present invention according to the embodiments of the present invention are given below. Note that titles or subtitles may be used in the examples for the convenience of a reader, which in no way should limit the scope of the invention. Moreover, certain theories are proposed and disclosed herein; however, in no way should they, whether they are right or wrong, limit the scope of the invention so long as the invention is practiced according to the invention without regard for any particular theory or scheme of action.

The following is an exemplary embodiment according to the disclosure.

EXAMPLE

In the following exemplary embodiment, an expandable scaffold is formed with the first material (i.e., the soft material) being polyurethane (PU) and the second material being nanosized hydroxyapatite (nHA) and bone particles. An additional material can be a sacrificial one (salt, sugar, fast dissolving/degrading polymers) that can be removed by immersion in water of other liquids or solvents.

Scaffold Fabrication:

Multiple methods of fabrications have been used and proved to work.

One such method is presented here: Firstly, composite sheets of PU-nHA were made according to weight ratio of 80% PU and 20% nHA. Two types of PU were used, including the D640 (HydroMed™ D640; AdvanSource Biomaterials; Wilmington, MA), and D3 (HydroMed™ D3; AdvanSource Biomaterials; Wilmington, MA). The two polymers were mixed in weight ratio of 80% D640 and 20% D3. The two polymers were dissolved in 60 ml of absolute ethanol (ACS regent grade, Fisher Scientific; Hampton, NH) and 5 ml of ultrapure deionized water (0.055 uS/18 MOhm, dispensed from a Siemens Lobster unit, Washington, DC) in a 125-ml screw-top flask. The nHA (BABIHAP-N100, 100 nm particle size, Berkeley Advanced Biomaterials; Berkeley, CA) was dispersed in ethanol and sonicated for 30 minutes in an ice bath. A stir bar was added, and then flask was put on a stirring and heating plate at 300 rpm and 45° C. for 2 days to be completely mixed. The mixture was then poured in silicon mold in a way that no air bubbles form inside the composites. Then, the mixture was dried by having the mold in the oven at 50° C. for 15 hours, and then left to cool at room temperature. The result is a film of two types of polyurethane [D640 and D3] with nHA, The ratio between these polymers can be varies from 0:100 to 100:0 wt. %. The PU-nHA film has a thickness of 0.28-0.31 mm.

Then, the PU-nHA film was cut into uniform rectangular pieces, each with a length of 45 mm and a width of 6.8 mm. These pieces were used to build the 3D scaffold.

Figure 3:
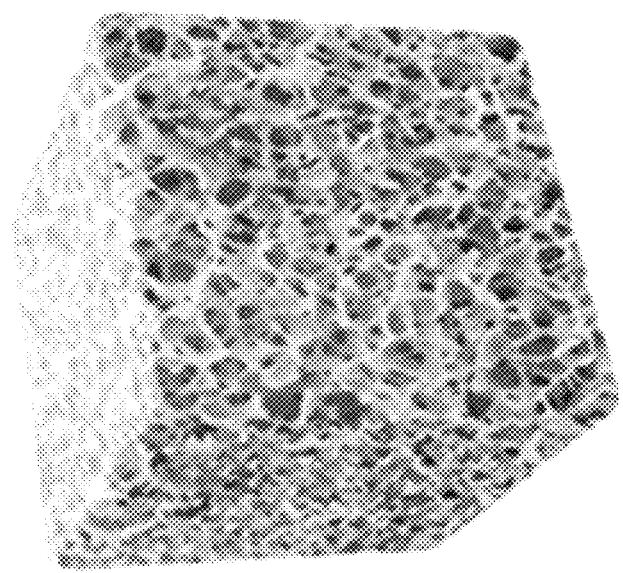
FIG. 3 shows a schematic view of an expandable scaffold according to one embodiment of the disclosure.

The 3D porous structure of the expandable scaffold was built layer-by-layer using the PU-nHA film and bone particles (IntrOss). FIG. 3 shows a schematic view of the expandable scaffold. As shown in FIG. 3, the expandable scaffold was designed to mimic the actual bone component of soft and hard component. The mass ratio of the hard material [nHA and bone particles (InterOss or BioOss, or similar)] and the soft material [PU] is 3/2, but it can be varied from 10000/0.01 to 0.01/10000. The bone was massed and distributed uniformly per iteration. 7 layers of the PU-nHA film with a total mass of 828.7 mg and 8 layers of bone particles with a total mass of 829 mg were built layer-by-layer to make the 3D porous structure of the expandable scaffold, and then the sample was left to dry at room temperature for 24 hours. It should be emphasized that the fabrication can be done by other methods, and is not limited thereto.

We have also fabricated the scaffolds by the following method as follows: the polymers D3/D640 were mixed in the desired ratios, as explained above. Then the nHA was mixed as explained above. Then the mixture, was brought to a desirable viscosity (ranging from 1 to over 500000 cP). At the desired viscosity, the bone particles (or the tricalcium phosphate, Calcium suphate, etc particles or the sacrificial material-salt, sugar, fast dissolving polymer or materials, or the mixtures of them) can be introduced in the desired ratios, as described above. The resulted mixture is uniformized and could be introduced into a mold and into a water bath. Then it can be dried (at varies conditions such as: under vacuum, under heat treatment, at room condition etc. and cut to shapes and sizes.

Scaffold Characterization:

Self-fitting:

The self-fitting property of the sample of the expandable scaffold was tested by making nonuniform defect in a hard PCV piece of material. The sample scaffold was loaded in the center of defect, and drops of deionized water was added as the liquid using a syringe to allow the scaffold to swell the water and expand. A camera was used to make images showing how the scaffold expands by swelling in the water to occupy the shape of defect.

Another test to the sample scaffold was done by making a nonuniform defect in a rubber, and then a dry sample scaffold was placed in the defect. Water was added, and the scaffold was left to swell in water to expand to occupy the shape of defect. A 3D laser microscopy was used to take images for dry scaffold, and 30 minutes after the scaffold immersed in DI water.

Water Uptake:

The scaffold absorption and swelling characterizations were evaluated in this example. The rate of water uptake by the sample scaffold in ultra-pure water were determined. A dry scaffold was first weighted, and then reading was taken at 0.5, 1, 2, 5, 10 and 30 minutes after the scaffold was placed in water. The mass of the initial dry sample scaffolds were 170-190 mg. The water uptake increase percent was calculated as:

$$\text{rate } \% = \frac{R_t - R_{initial}}{R_{initial}} * 100\% \qquad (1)$$

where $R_t$ is the measurement at each chosen time point, and $R_{initial}$ is initial or dry mass thereof.

Thermogravimetric Analysis (TGA):

The mass composition percentage of hard/soft material ratio was tested using the thermogravimetric analysis utilizing the differences in thermal decomposition of the scaffold components. The hard material of the sample scaffold decomposes at higher temperature than the soft material. The scaffold samples with an average weight of 24 mg were placed in crucible, and then the crucible was put in a Matter Toledo TGA-DSC 3+ instrument. The temperature was raised from 25° C. to 850° C. at a rate of 10° C./min and an air flow rate of 50 ml/min. The mass percentage change vs temperature was recorded and analyzed.

Surface Area Analysis:

Nitrogen absorption/desorption techniques were used to find the pore size and surface area of the sample scaffold. The sample scaffold was placed in a glass vessel, and then the scaffold was degassed at 35° C. for at least 8 hours. By the meaning of Nitrogen adsorption-desorption isotherm and utilizing the Brunauer-Emmett-Teller (BET) method, the scaffold surface area was evaluated. Similarly, the Barrett, Joyner, and Halenda (BJH) method was used to calculate the pore size/volume. The ASAP 2020 software suite was used in this analysis.

Three-Dimensional Laser Microscopy:

A laser scanning confocal microscope (LSCM, VK-X260K, Keyence, USA) was used to study the scaffold morphology by utilizing the Keyence's Multi-File Analyzer software for analysis of the 3D measurement data of sample cross section. The samples were tested in dry and wet condition with an 5× lens. For wet test samples, the scaffold samples were placed in DI water for 30 minutes, and then the samples were removed from the water, and the excess water was taken from the scaffold by tissue followed by imaging.

Micro-CT:

The bone and void space content of the scaffold was studied using micro-computed tomography (micro-CT, Scanco Medical μCT 40). The scaffold was placed in 20 ml of DI water for at least 24 hours prior to scanning. Triplicate scans were performed at 55 kVp, 145 μA (medium resolution, 12 μm voxel, calibrated to 1200 mg HA/cm).

Result and Discussion:

The expandable scaffold was made by using layer-by-layer method, which has the hard material of nHA and macro-sized bone particles that give the scaffold a nano/macro structure, making the scaffold suitable to use as a platform for osteogenesis. The scaffold characterizes in term of self-fitting properties, composition, porosity, topography.

The scaffold was designed to occupy and take the shape the defect. The process start when the scaffold swells in the fluids available in the body (by taking fluids 450% times its weight). The swelling process was associated with expansion in the scaffold volume (3.62 times its original volume, stdv 0.2019). The hydrophilic polymer continent of the scaffold provides the scaffold with its high water uptake rate and volume expansion. Mainly, the polyurethane polymer [D640, 80% from total polymer mass] that has high linear expansion [100.44%] was used for that purpose. This high linear expansion and high water uptake make the scaffold adopt like a jelly structure, which assists the scaffold in taking the defect shape during the expansion. However, this feature creates difficulties to keep the scaffold structure after swelling. Therefore, it was mixed with another polyurethane polymer [D3], which has the linear expansion of 42.11%, to provide more structure stability for the wet scaffold. Different ratios of D640/D3 were examined to obtain a maximum volume expansion and at the same time maintain the scaffold structure. Starting from a D640/D3 mass ratio of 1/1, 3/2, 4/1 and 9/1, the first two ratios show low volume expansion. The 9/1 ratio scaffold starts to lack in structure cohesion. The optimum ratio was found to be the 4/1 ratio. The hard, nonorganic materials of this scaffold are InerOss® bone particles and nHA.

The ratio of the hard/soft materials was studied, and the optimum hard/soft ratio was found to be is 3/2. However, higher ratios of the hard/soft materials show a low scaffold interconnection.

Figure 4:
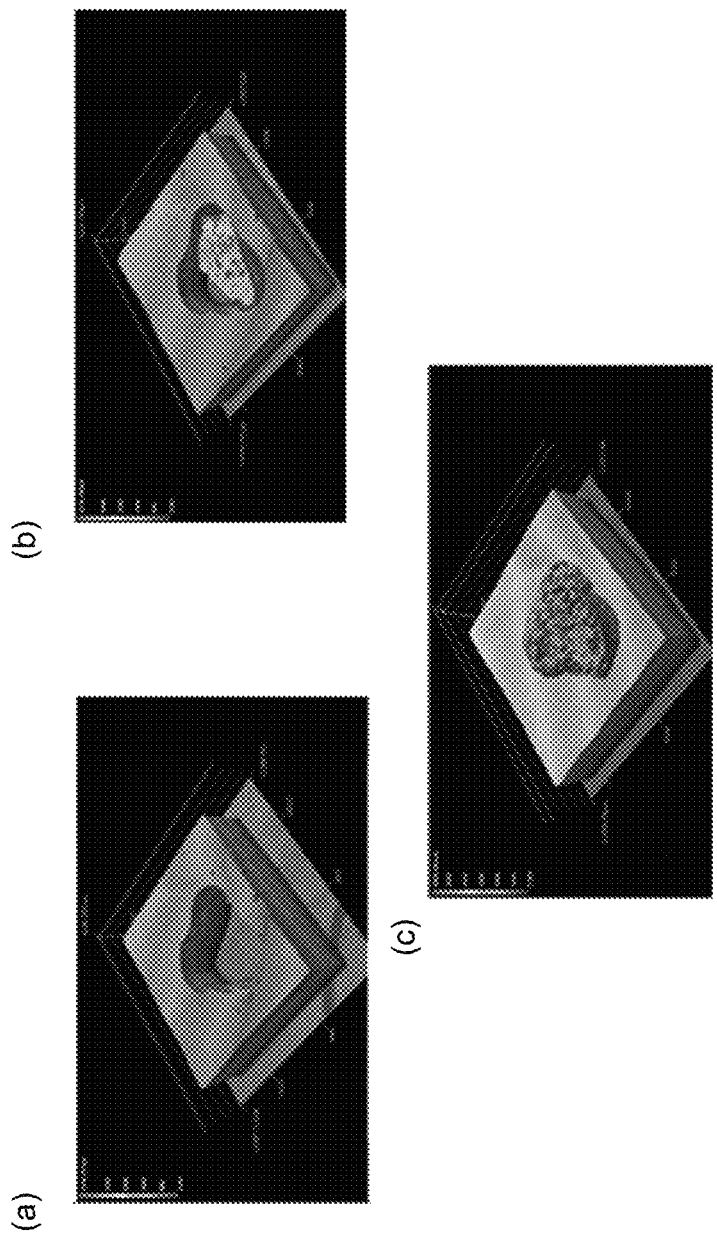
FIG. 4 shows 3D laser microscopy of the expandable scaffold according to one embodiment of the disclosure, where (a) represents an image of a non-uniform bone defect, (b) shows the expandable scaffold being implanted or positioned inside the defect before hydration, and (c) shows the scaffold expanding and filling up the volume of the defect after the hydration.

The self-fitting behavior of the scaffold was proved by making a nonuniform defect in a rubber. A dry sample of the scaffold was placed in the defect, water was added, and the scaffold was left to swell in water and expand to occupy the shape of defect. A 3D laser microscopy was used to take images for the dry scaffold, and then the scaffold was immersed in DI water for one hour. Then it was taken from water, wiped to remove the excess water, and 3D microscopy images were taken. FIG. 4 shows 3D laser microscopy of the expandable scaffold according to one embodiment of the disclosure, where (a) represents an image of a non-uniform bone defect, (b) shows the expandable scaffold being implanted or positioned inside the defect before hydration, and (c) shows the scaffold expanding and filling up the volume of the defect after the hydration. All images as shown in FIG. 4 are top views of the defect with a 5× lens. As shown in FIG. 4, the 3D image analysis of wet and dry scaffold shows that the wet scaffold volume become 3.62 times the dry scaffold.

Figure 5:
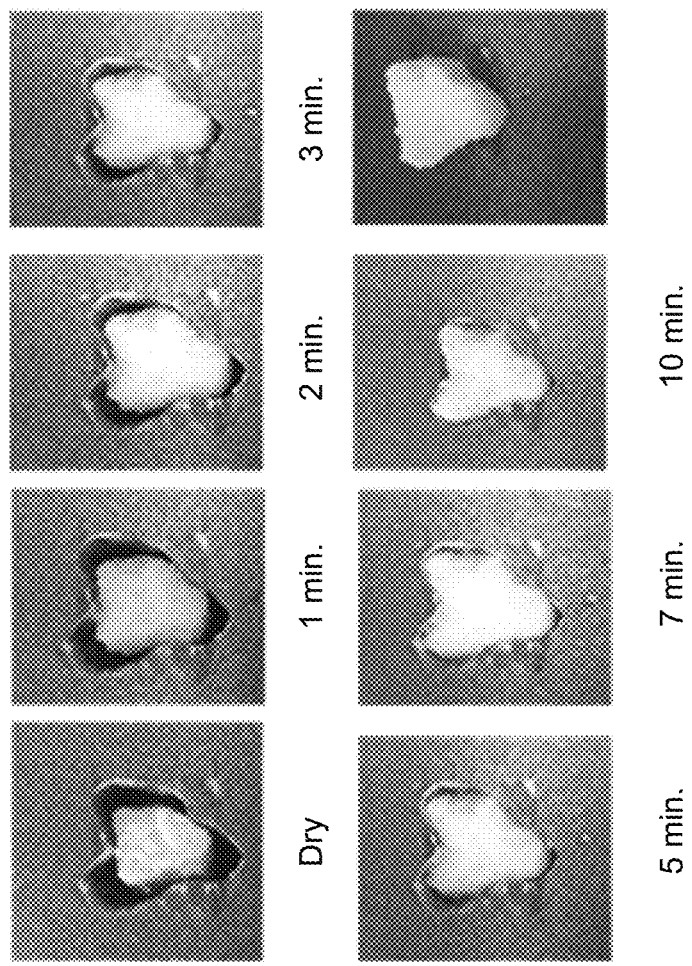
FIG. 5 shows images of the expandable scaffold in a self-fitting test inside a PVC mold taken at different times after swelling started according to one embodiment of the disclosure.

Another self-fitting test was done to show time line of expansion, in which a camera was used to take the pictures proving the concept of self-fitting of the expandable scaffold. FIG. 5 shows images of the expandable scaffold in a self-fitting test inside a PVC mold taken at different times after swelling started according to one embodiment of the disclosure. As shown in FIG. 5, the images taken after 1, 2, 3, 5, 7 and 10 minutes from the swelling start demonstrate the expansion as function of time.

Figure 6:
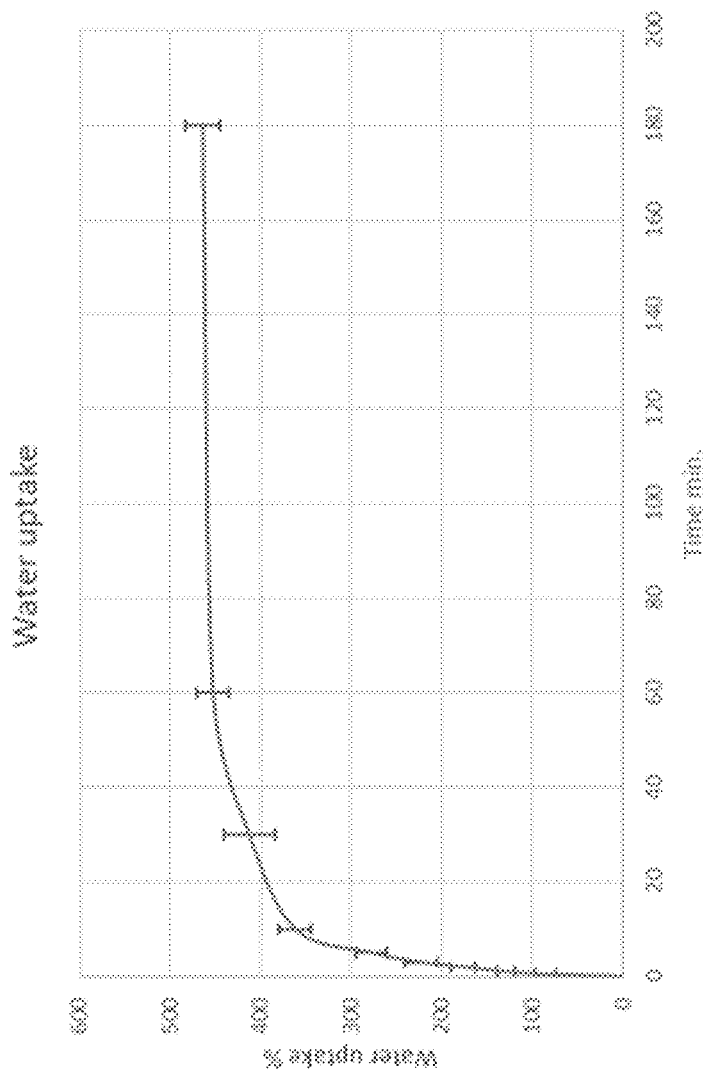
FIG. 6 shows a chart of the swelling plot of the expandable scaffold according to one embodiment of the disclosure, where three samples were tested.

FIG. 6 shows a chart of the swelling plot of the expandable scaffold according to one embodiment of the disclosure, where three samples were tested. For each sample, the dry sample was weighted first, and was then immersed in DI water. The samples were removed from the DI water, and after removal of the excess of water from the samples using tissues, the samples were weighted, and the average of the three readings were recorded and plotted with time, with standard error being recorded at each measurement point. As shown in FIG. 6, in the first 10 minutes, a high and linear increase is shown in water uptake % where the scaffold absorbs 370% of its dry weight. After 10 minutes, the water uptake % decreases significantly. After one hour, the water uptake approximately remains constant.

Figure 7:
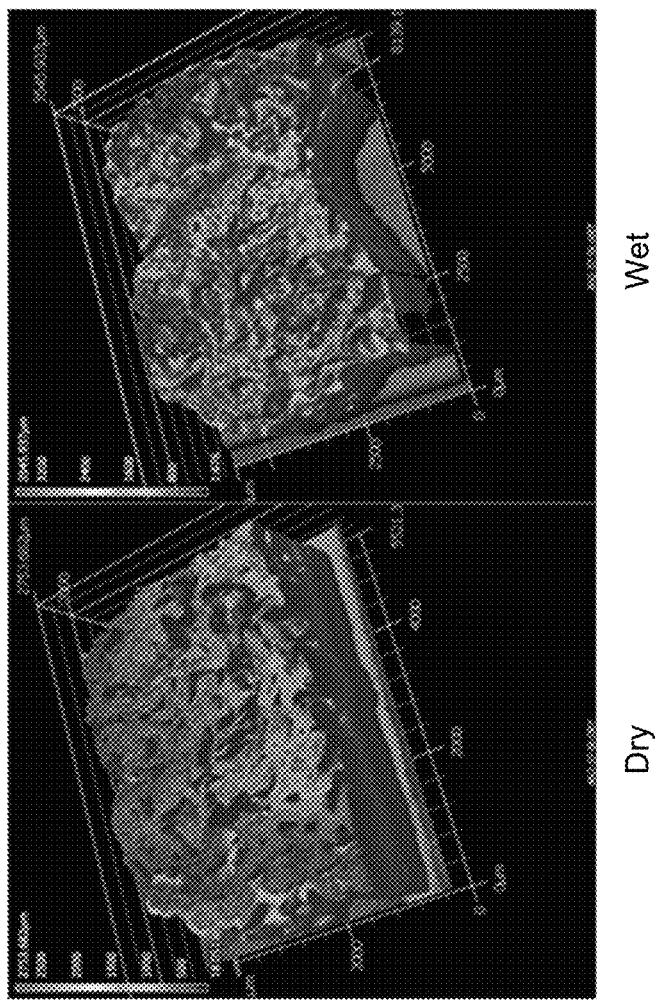
FIG. 7 shows 3D laser microscopy images of cross sections a dry scaffold and a wet scaffold according to one embodiment of the disclosure.

FIG. 7 shows 3D laser microscopy images of cross sections a dry scaffold and a wet scaffold according to one embodiment of the disclosure. The images as shown in FIG. 7 demonstrate the expansion due to water absorption, and present porosity of the scaffold in wet and dry conditions. The assessment exhibit weight increase of 450% of dry weight as shown in FIG. 7. The high-water uptake can attribute to hydrophilic nature of the polymer resulted from the hydrogen bonding interaction between water molecules and the PEG and the porous structure of the scaffold.

The change in the dimension of the expandable scaffold after it was immersed in water was evaluated over a period of 30 minutes. The change in volume was recorded to evaluate the scaffold size for the in vivo implantation. To determine the volume change, the images from 3D laser microscopy as shown in FIG. 7 were used to compare between the dry sample and the wet sample 30 minutes after it was immersed in DI water. The 3D image analysis of the wet and dry scaffold shows that the volume of the wet scaffold becomes 3.62 times the volume of the dry scaffold. The top view of the scaffold slice image shows the expansion in that plane. The wet sample image shows nonuniform deformation during the expansion, which makes the scaffold able to take the shape of a defect that the scaffold is disposed therein. Furthermore, the images can show pores on the sample surface, and in the wet scaffold, the pores appear larger than the dry scaffold.

Figure 8:
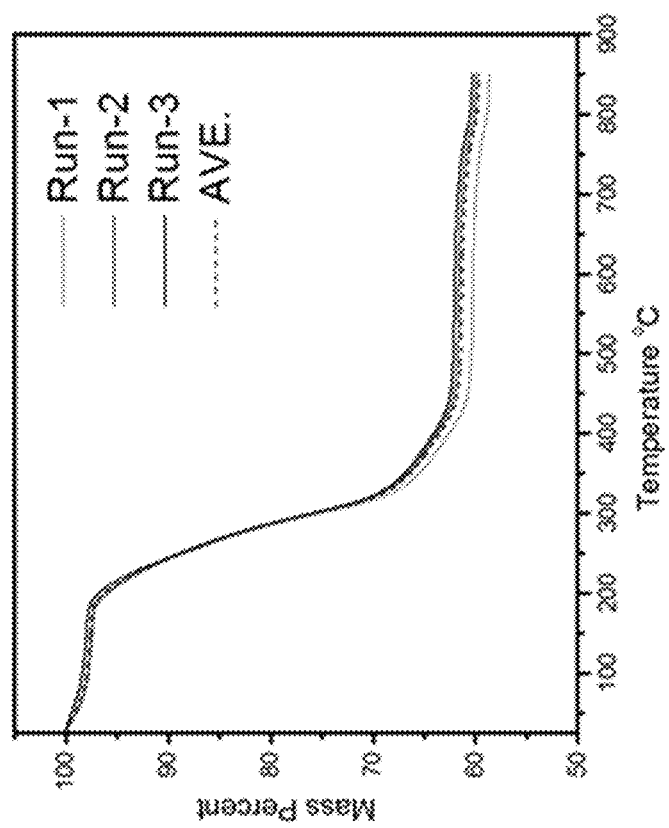
FIG. 8 shows a chart of the thermogravimetry curve for three scaffold samples according to one embodiment of the disclosure.

The expandable scaffold is designed to mimic the natural component of bone tissue. Among the hard inorganic material and the soft organic material, the soft material is elastic and thermally unstable, while the mineral inorganic hard material is stiffer and has higher thermal stability. FIG. 8 shows a chart of the thermogravimetry curve for three scaffold samples according to one embodiment of the disclosure. As shown in FIG. 8, three samples were subjected to the TGA test to detect the ratios of the scaffold mass components. In the thermographic process, the furnace temperature increases, which causes the material to thermally decompose by combustion, and the soft/hard materials of the scaffold will decompose at different temperatures. The soft material (polymer) of the scaffold decomposes first due to its low thermal satiability, where 40% of scaffold mass was expected to be removed, leaving the 60% of the mineral hard material of nHA and bone particles. The mass percent-temperature curve as shown in FIG. 8 shows that the water mass losses is 2.56% of the total mass of the scaffold, followed by the PU mass losses, leaving the bone particles and nHA, where the bone particles thermally decompose at the temperature higher than 650° C. The TGA analysis shows the that the average of the hard material of the scaffold is 61.69%, which agrees with the theoretical mass ratio assumed in fabrication [60%].

Nitrogen adsorption isotherm was utilized to determine the pore volume and pore size for the scaffold. The result shows that the BET service area is 16.3244 m$^2$/g, the BJH average pore size (diameter) is 251.154 Å, and the BJH cumulative pores volume is 0.11793 cm$^3$/g.

Figure 9:
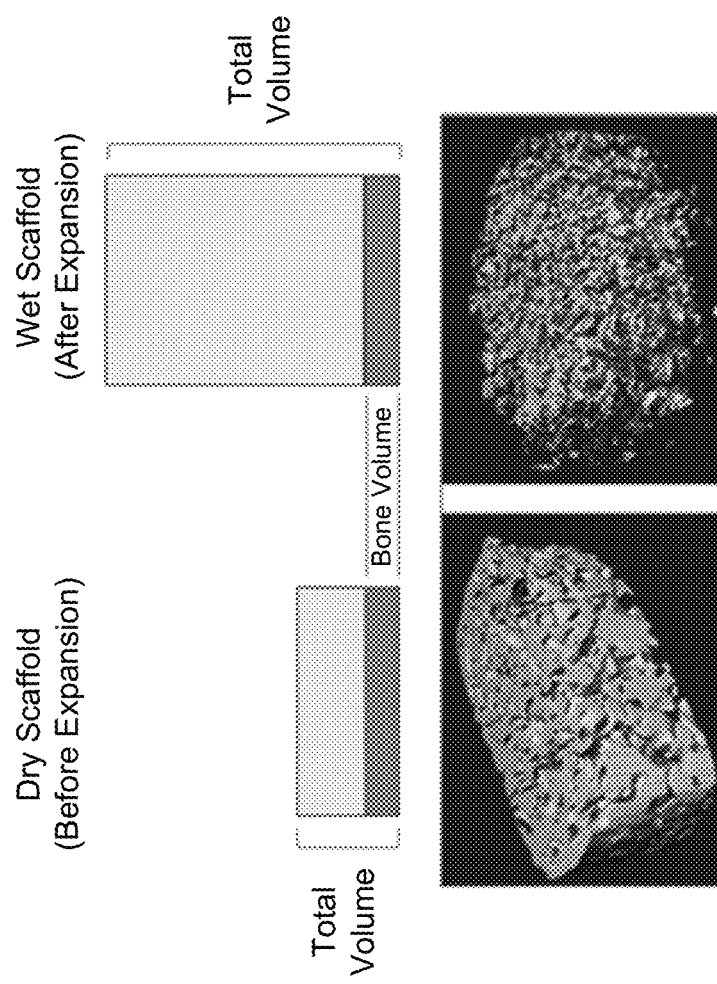
FIG. 9 shows micro-CT scan images for dry and wet scaffold samples according to certain embodiments of the disclosure.

Micro-CT was used to study the bone particles size and distribution within the scaffold matrix. FIG. 9 shows micro-CT scan images for dry and wet scaffold samples according to certain embodiments of the disclosure. As shown in FIG. 9, a bar graph represents the bone to total volume fraction in the wet and dry scaffold, and a relatively uniform distribution of bone particles appeared in the scaffold. The images of bone particles distributing in the scaffold in the dry scaffold before and after expansion are shown in FIG. 9. The bone-to-total volume ratio (BV/TV) of the dry scaffold (before expansion) is 51%, while the BV/TV for the wet scaffold (after expansion) is 0.14%. The bone to total volume ratio decreases after expansion, where the polymer contained in the scaffold is responsible for volume expansion. Specifically, the calculation is provided as follows:

$$\frac{BV}{BT_d} = 0.51 \tag{2}$$

$$\frac{BV}{BT_w} = 0.14 \tag{3}$$

where BV represents the bone volume, BTd represents the total dry volume of the scaffold (before expansion), and BTw represents the total wet volume of the scaffold (after expansion).

Substituting the equation (3) in the equation (2), the following equation is obtained:

$$\frac{BT_w}{BT_d} = 3.642 \tag{4}$$

The volume expansion from the three-dimension laser macroscopy was 3.62, which agree with the result from the result of the micro-CT (3.642).

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments are chosen and described in order to explain the principles of the disclosure and their practical application so as to activate others skilled in the art to utilize the disclosure and various embodiments and with various modifications as are suited to the particular use contemplated. Alternative embodiments will become apparent to those skilled in the art to which the present disclosure pertains without departing from its spirit and scope. Accordingly, the scope of the present disclosure is defined by the appended claims rather than the foregoing description and the exemplary embodiments described therein.

REFERENCE LIST

[1]. Al-namnam, N. M., Govindan, M., Lin, W., Oon, K., Hwi, K., Huat, C., & Cheong, W. (2017). An injectable poly(caprolactone trifumarate-gelatin microparticles) (PCLTF-GMPs) scaffold for irregular bone defects: Physical and mechanical characteristics. Materials Science & Engineering C, 72, 332-340. https://doi.org/10.1016/j.msec.2016.11.086

[2]. Albrektsson, T., & Johansson, C. (2001). and osseointegration, 96-101.

[3]. Ceramics, M., & Dubok, V. A. (2001). Bioceramics—Yesterday, Today, Tomorrow.pdf (Vol. 39, pp. 381-394).

[4]. Guelcher, S. A. (2008). Biodegradable Polyurethanes: Synthesis and Applications in Regenerative Medicine. Tissue Engineering Part B: Reviews, 14 (1), 3-17. https://doi.org/10.1089/teb.2007.0133

[5]. Hench, L. L., & Thompson, I. (2010). Twenty-first century challenges for biomaterials. Journal of the Royal Society Interface, 7 (SUPPL. 4). https://doi.org/10.1098/rsif.2010.0151.focus

[6]. Hollister, S. J. (2005). No TitlePorous scaffold design for tissue engineering. Nature Materials, 4, 518-524. Retrieved from http://dx.doi.org/10.1038/nmat1421

[7]. Hutmacher, D. W. (2000). Scaffolds in tissue engineering bone and cartilage. The Biomaterials Silver Jubilee Compendium (Vol. 21). Woodhead Publishing Limited. https://doi.org/10.1016/B978-008045154-1.50021-6

[8]. Iqbal, M., & Xiaoxue, S. Æ. (2009). A review on biodegradable polymeric materials for bone tissue engineering applications, 5713-5724. https://doi.org/10.1007/s10853-009-3770-7

[9]. Jackson, B. K., Bow, A. J., Kannarpady, G., Biris, A. S., Anderson, D. E., Dhar, M., & Bourdo, S. E. (2018).

Polyurethane/nano-hydroxyapatite composite films as osteogenic platforms. Journal of Biomaterials Science, Polymer Edition, 29 (12), 1426-1443. https://doi.org/10.1080/09205063.2018.1464264
[10]. Laurencin, C. T., Ambrosio, A. M. A., Borden, M. D., & Cooper, J. A. (1999). Tissue Engineering: Orthopedic Applications, 19-46.
[11]. Li, Y., Chen, S., Li, L., & Qin, L. (2015). ScienceDirect Bone defect animal models for testing efficacy of bone substitute biomaterials. https://doi.org/10.1016/j.jot.2015.05.002
[12]. Nail, L. N., Zhang, D., Reinhard, J. L., & Grunlan, M. A. (2015). Fabrication of a Bioactive, PCL-based "Self-fitting" Shape Memory Polymer Scaffold, (October), 1-8. https://doi.org/10.3791/52981
[13]. Nedomová, B., Budáčová, J., Frištáková, M., & Šagát, T. (2016). Arthrogryposis multiplex congenita z pohl'adu anestéziológa. Lekarsky Obzor, 65 (12), 354-359. https://doi.org/10.1002/jor
[14]. Qutachi, O., Vetsch, J. R., Gill, D., Cox, H., Scurr, D. J., Hofmann, S., . . . Rahman, C. V. (2014). Acta Biomaterialia Injectable and porous PLGA microspheres that form highly porous scaffolds at body temperature, 10, 5090-5098. https://doi.org/10.1016/j.actbio.2014.08.015
[15]. Rasperini, G., Pilipchuk, S. P., Flanagan, C. L., Park, C. H., Pagni, G., Hollister, S. J., & Giannobile, W. V. (2014). 3D-printed Bioresorbable Scaffold for Periodontal Repair. Journal of Denal Reseach, 94 (9), 153-157. https://doi.org/10.1177/0022034515588303
[16]. Rousseau, M., Anderson, D. E., Lillich, J. D., Apley, M. D., Jensen, P. J., & Biris, A. S. (2014). In vivo assessment of a multicomponent and nanostructural polymeric matrix as a delivery system for antimicrobials and bone morphogenetic protein-2 in a unicortical tibial defect in goats, 75 (3).
[17]. Senatov, F. S., Zadorozhnyy, M. Y., Niaza, K. V, Medvedev, V. V, Kaloshkin, S. D., Anisimova, N. Y., . . . Yang, K. (2017). Shape memory e ff ect in 3D-printed sca ff olds for self-fi tting implants, 93 (May), 222-231. https://doi.org/10.1016/j.eurpolymj.2017.06.011
[18]. Senturk, B., Cubuk, M. O., Ozmen, M. C., Aydin, B., Guler, M. O., & Tekinay, A. B. (2016). Inhibition of VEGF mediated corneal neovascularization by anti-angiogenic peptide nanofibers. Biomaterials. https://doi.org/10.1016/j.biomaterials.2016.08.045
[19]. Xie, R., Hu, J., Hoffmann, O., Zhang, Y., Ng, F., Qin, T., & Guo, X. (2018). Self-fitting shape memory polymer foam inducing bone regeneration: A rabbit femoral defect study. https://doi.org/10.1016/j.bbagen.2018.01.013
[20]. Xie, R., Hu, J., Ng, F., & Tan, L. (2016). High performance shape memory foams with isocyanate-modified hydroxyapatite nanoparticles for minimally invasive bone regeneration. Ceramics International. https://doi.org/10.1016/j.ceramint.2016.11.216
[21]. Zhang, D., George, O. J., Petersen, K. M., Jimenez-vergara, A. C., Hahn, M. S., & Grunlan, M. A. (2014). Acta Biomaterialia A bioactive "'self-fitting'" shape memory polymer scaffold with potential to treat craniomaxillo facial bone defects. ACTA BIOMATERIALIA, (August). https://doi.org/10.1016/j.actbio.2014.07.020

What is claimed is:

1. An expandable scaffold, comprising:
a three-dimensional (3D) porous structure comprising a composite material composed by a first material and a second material,
wherein the first material comprises a mixture of a first biocompatible and biodegradable polyurethane polymer having a linear expansion of 100.44%, and a second biocompatible and biodegradable polyurethane polymer having a linear expansion of 42.11%, wherein a mass ratio of the first biocompatible and biodegradable polyurethane polymer to the second biocompatible and biodegradable polyurethane polymer is in a range from 1/1 to 9/1;
wherein the 3D porous structure has a tunable expansion capacity, and when applied in a liquid, is configured to uptake the liquid and expand from an original volume to an expansion volume up to 10000 times of the original volume; and
wherein a mass ratio of the second material to the expandable scaffold is equal to or greater than 60%.

2. The expandable scaffold of claim 1, wherein the 3D porous structure is formed by a plurality of layers of the composite material, and the layers of the composite material are arranged in accordance with a shape and a size of the expansion volume.

3. The expandable scaffold of claim 1, wherein the liquid is water or bodily fluid of a living subject.

4. The expandable scaffold of claim 3, wherein the 3D porous structure, when disposed in a bone defect or a tissue defect of the living subject, uptakes bodily fluid of the living subject and expands to self-fit in the bone defect or the tissue defect.

5. The expandable scaffold of claim 3, wherein the expandable scaffold is disposed inside or around an implantable carrier, and the implantable carrier is disposed at a location within the living subject.

6. The expandable scaffold of claim 3, wherein the 3D porous structure is formed by injecting the composite material into a bone defect or a tissue defect of the living subject using an application device, such that the injected composite material uptakes bodily fluid of the living subject and expand to self-fit in the bone defect or the tissue defect.

7. The expandable scaffold of claim 6, wherein the application device is a syringe.

8. The expandable scaffold of claim 1, wherein the expandable scaffold is loaded with a plurality of cells, drugs, antibiotics, growth factors or proteins.

9. The expandable scaffold of claim 1, wherein the second material is selected from a group consisting of hydroxyapatite, apatite, bone particles, calcium phosphate family or particles of multiple phases, calcium sulfate family or particles of multiple phases, graphitic materials, graphene, carbon nanotubes, carbon spheres, gold, silver nanomaterials, magnesium, zinc, and a combination thereof.

10. The expandable scaffold of claim 9, wherein the second material is nanosized hydroxyapatite (nHA).

11. The expandable scaffold of claim 10, wherein external and internal surfaces of the 3D porous structure, and/or a bulk of the 3D porous structure have a surface coating.

12. The expandable scaffold of claim 11, wherein a thickness of the surface coating ranges from 0.001 nm to 10 cm.

13. The expandable scaffold of claim 11, wherein the surface coating is formed of a biocompatible and biodegradable polymer material, comprising: (poly($\alpha$-esters), polyglycolide, polylactide, poly(L-lactic acid)(PLLA), poly(D-lactic acid) (PDLA), poly(D,L-lactic acid)(PDLLA), poly(lactide-co-glycolide), polyhydroxyalkanoates, poly(3-hydroxybutyrate), PHBV, Polycaprolactone(PCL), Poly (propylene fumarate)(PPF), polyanhydrides, polyacetals, poly(ortho esters), polycarbonates, poly(trimethylene carbonate)(PTMC), poly(desaminotyrosyltyrosine alkyl ester carbonates)(PDTEs), polyurethanes, polyphosphazenes, (poly[bis(trifluoroethoxy)phosphazene], polyphosphoesters, poly(ester ether)s, polydioxanone (PDO), poly(β-amino esters)(PBAEs), poly(anhydride ester)s, poly(ester urethane)s, urethanes, polyurethanes, poly(ethylene glycol) (PEG), poly(propylene glycol)(PPG), triblock pluronic ([PEG]n-[PPG]m-[PEG]n), pluronic, PEG diacrylate (PEGDA), PEG dimethacrylate (PEGDMA), collagen, elastin, elastin-like polypeptides (ELPs), aAlbumin, fibrin, natural poly(amino acids), poly(γ-glutamic acid), poly(L-lysine), synthetic poly(amino acids), poly(L-glutamic acid), poly (aspartic acid), poly(aspartic acid)(PAA), polysaccharides, hyaluronic acid (HA), chondroitin sulfate (CS), polycaprolactone (PCL), chitin, chitosan, alginate, dextran, collagen, agarose, mannan or inulin.

14. The expandable scaffold of claim 10, wherein the expandable scaffold is designed to have a non-uniform density and packing density.

15. The expandable scaffold of claim 10, wherein the 3D porous structure has a porosity ranging from 1% to 99%.

16. The expandable scaffold of claim 10, wherein construction of the expandable scaffold is done by 3D bioprinting and hybrid printing and deposition technology by layer-by-layer deposition.

17. A bone regeneration system, comprising:
the expandable scaffold of claim 1, configured to be disposed at a location within a living subject in which bone formation and regeneration are required, such that the 3D porous structure of the expandable scaffold uptakes bodily fluid of the living subject and expands at the location within the living subject, wherein the second material includes bone particles.

18. The bone regeneration system of claim 17, wherein the expandable scaffold is disposed in a bone defect of the living subject, such that the 3D porous structure of the expandable scaffold uptakes the bodily fluid of the living subject and expands to self-fit in the bone defect.

19. The bone regeneration system of claim 17, wherein the expandable scaffold is disposed inside or around an implantable carrier, and the implantable carrier is disposed at the location within the living subject.

20. The bone regeneration system of claim 17, further comprising an application device configured to inject the composite material into the location within the living subject, such that the injected composite material uptakes bodily fluid of the living subject and expand to form the expandable scaffold.

21. The bone regeneration system of claim 20, wherein the application device is a syringe.

22. A soft tissue regeneration system, comprising:
the expandable scaffold of claim 1, configured to be disposed within a tissue defect of a living subject in which soft tissue formation and regeneration are required, such that the 3D porous structure of the expandable scaffold uptakes bodily fluid of the living subject and expands to self-fit in the tissue defect.

23. The soft tissue regeneration system of claim 22, wherein the soft tissue of the living subject includes muscle, skin, nerve, blood arteries and vessels of the living subject.

24. A bleed stopping device, comprising:
the expandable scaffold of claim 1, configured to be disposed at a location of a living subject in which bleeding occurs, such that the 3D porous structure of the expandable scaffold uptakes blood of the living subject and expands to stop the bleeding.

25. An expandable scaffold, comprising:
a three-dimensional (3D) porous structure comprising a composite material composed by a first material and a second material,
wherein the first material comprises a mixture of a first biocompatible and biodegradable polyurethane polymer having a linear expansion of 100.44%, and a second biocompatible and biodegradable polyurethane polymer having a linear expansion of 42.11%, wherein a mass ratio of the first biocompatible and biodegradable polyurethane polymer to the second biocompatible and biodegradable polyurethane polymer is in a range from 1/1 to 9/1; and
wherein the 3D porous structure has a tunable expansion capacity, and when applied in a liquid, is configured to uptake the liquid and expand from an original volume to an expansion volume up to 10000 times of the original volume.

* * * * *